(12) United States Patent
Liu et al.

(10) Patent No.: US 8,722,604 B2
(45) Date of Patent: May 13, 2014

(54) STABLE LIQUID CLEANSING COMPOSITIONS COMPRISING CRITICAL WINDOW OF PARTIALLY HYDROGENATED TRIGLYCERIDE OIL OF DEFINED IODINE VALUE

(75) Inventors: Hongjie Liu, Shelton, CT (US); Liang Sheng Tsaur, Norwood, NJ (US); Jamie Lynn Miler, New Haven, CT (US); Tirucherai Varahan Vasudevan, Bethany, CT (US); Virgilio Barba Villa, Ermerson, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 664 days.

(21) Appl. No.: 12/904,594

(22) Filed: Oct. 14, 2010

(65) Prior Publication Data
US 2012/0094885 A1 Apr. 19, 2012

(51) Int. Cl.
*A61Q 19/10* (2006.01)
*A61K 8/18* (2006.01)
*A61K 8/00* (2006.01)
*C11D 17/00* (2006.01)

(52) U.S. Cl.
USPC ............ 510/159; 510/119; 510/130; 510/155

(58) Field of Classification Search
USPC .................... 510/159, 119, 130, 155
See application file for complete search history.

(56) References Cited

U.S. PATENT DOCUMENTS

| | | | |
|---|---|---|---|
| 3,723,325 | A | 3/1973 | Parran, Jr. |
| 4,565,647 | A | 1/1986 | Llenado |
| 5,009,814 | A | 4/1991 | Kelkenberg et al. |
| 5,389,279 | A | 2/1995 | Au et al. |
| 6,395,690 | B1 | 5/2002 | Tsaur |
| 2002/0012697 | A1 | 1/2002 | Schwartz |
| 2004/0234467 | A1 | 11/2004 | Ananthapadmanabhan et al. |
| 2004/0234468 | A1 | 11/2004 | Kerschner et al. |
| 2004/0234469 | A1 | 11/2004 | O'Connor et al. |
| 2004/0234558 | A1 | 11/2004 | O'Connor et al. |
| 2004/0235691 | A1 | 11/2004 | Pham et al. |
| 2005/0281851 | A1 | 12/2005 | Cap |
| 2008/0081776 | A1* | 4/2008 | Crotty et al. .................. 510/130 |
| 2009/0012177 | A1 | 1/2009 | Shafa |

FOREIGN PATENT DOCUMENTS

| | | |
|---|---|---|
| CA | 2678768 | 8/2009 |
| EP | 0348976 A2 | 1/1990 |
| EP | 1479365 | 11/2004 |
| EP | 1479378 | 11/2004 |
| WO | WO9932069 | 7/1999 |
| WO | 2004/017745 | 3/2004 |
| WO | WO2004017745 A1 | 3/2004 |
| WO | WO2009064023 A1 | 5/2009 |

OTHER PUBLICATIONS

Co-pending Application for Applicant. Liu et al.; U.S. Appl. No. 12/371,050, filed Feb. 13, 2009, entitled: Personal Wash Composition Comprising Specific Blends of Saturation (Hydrogenated) Oil to Unsaturated Triglyceride.
Co-pending Application for Applicant Liu et al.; U.S. Appl. No. 12/904,571, filed Oct. 14, 2010, entitled: Stable Liquid Cleansing Compositions Comprising Critical Window of Hydrogenated Triglyceride Oils.
PCT International Search Report PCT/EP2011/066926 dated Jul. 3, 2012 with Written Opinion.
Internet website article from Welch House Clark on "Refined Soybean Oil".

* cited by examiner

*Primary Examiner* — Ling Choi
*Assistant Examiner* — Thuy-Ai Nguyen
(74) *Attorney, Agent, or Firm* — Ronald A. Koatz

(57) ABSTRACT

The present invention provides personal wash compositions where partially hydrogenated triglyceride oil (defined by IV of 20 to 100) are specifically formulated to provide low temperature stability. Specifically when formulated to have specific concentration of partially hydrogenated triglycerides, delivered alone or as part of mixture with other oils, desirable low temperature stability of formulations is achieved.

5 Claims, 2 Drawing Sheets

LINEAR CORRELATION OF MELTING ENTHALPY OF HSBO/SBO OIL MIXTURE AND AMOUNT OF HYDROGENATED SOYBEAN OIL IN THE MIXTURE (CRYSTALLINITY).

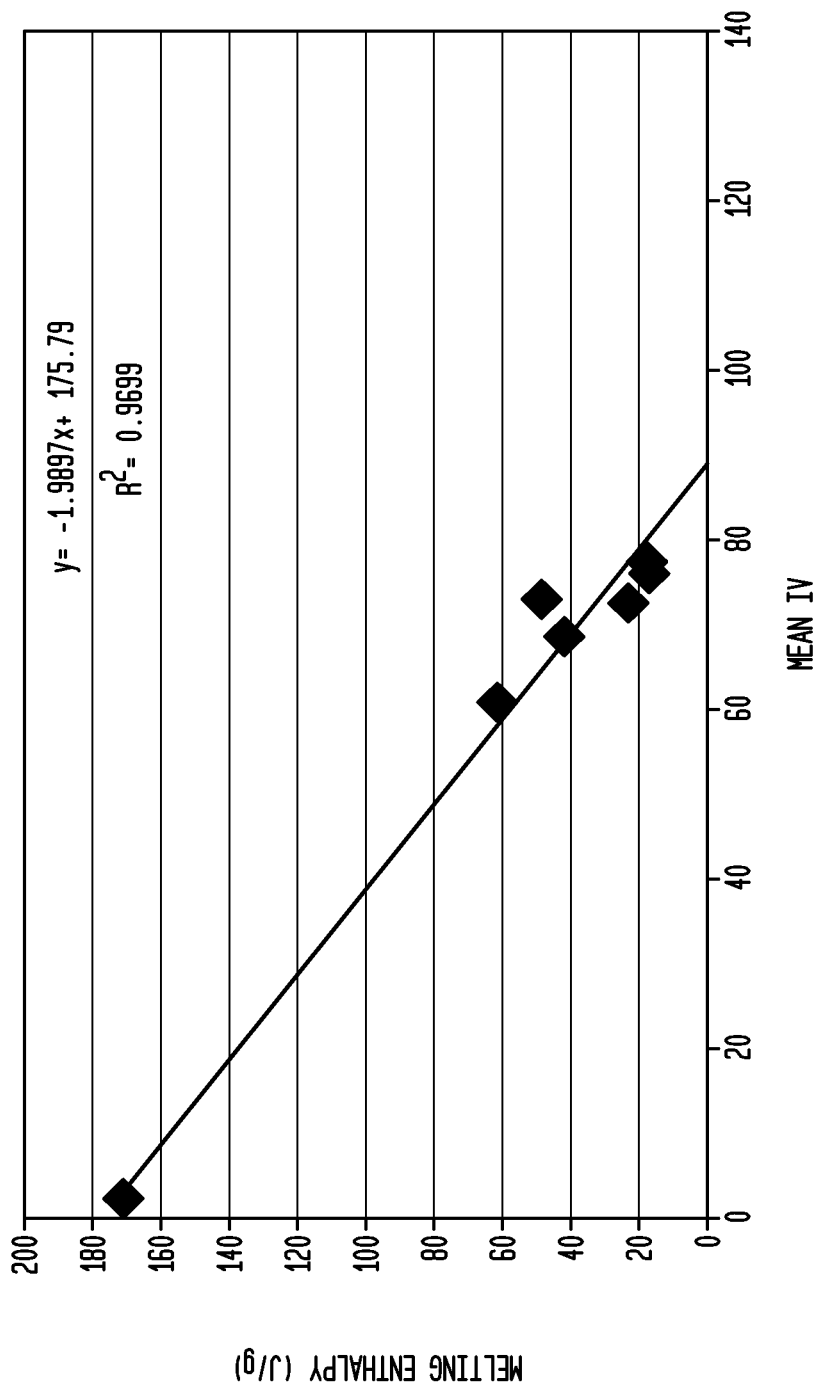

STABLE LIQUID CLEANSING COMPOSITIONS COMPRISING CRITICAL WINDOW OF PARTIALLY HYDROGENATED TRIGLYCERIDE OIL OF DEFINED IODINE VALUE

FIELD OF THE INVENTION

The present invention relates to stable liquid personal wash compositions comprising both long chain fatty acids (used to provide skin functional benefits like to mildness and moisturization) and partially hydrogenated triglycerides of defined IV value and/or mixtures of partially hydrogenated triglycerides of defined IV values and other oils. The partially hydrogenated triglycerides (defined by iodine value IV value of 40 to 100, preferably 50 to 90) stabilize the compositions over a wide range of storage temperatures. More specifically, the partially hydrogenated triglyceride and mixtures of such with other oil prevent low temperature composition instability caused by high melting point components (long chain fatty acids, for example) found in the liquid cleansing formulations. Use of critical amounts (e.g., minimum amount within defined IV window to provide sufficient crystallinity to stabilize liquids) of partially hydrogenated triglyceride in liquid personal wash compositions is believed unknown.

The partially hydrogenated triglyceride may be introduced into formulations as a single component (e.g., partially hydrogenated soybean oil) of defined IV or as a mixture with other oils (e.g., sunflower seed oil) as long as the partially hydrogenated oil of defined IV is used in amounts required as a percentage of fully formulated personal wash compositions.

This amount is required to ensure the viscosity of the composition retains at least a defined certain percentage of its original viscosity (e.g., greater than 70%, preferably 75% or greater, even more preferably, 80% or greater of its original viscosity) following cold storage conditions (e.g., after kept at 4° C. for a one week period).

Measurement of the degree of saturation, whether partially hydrogenated triglyceride is introduced alone or as a mixture with other oils, can be conducted by thermal analysis of phase transition (melting or crystallization), crystallinity analysis (e.g., Differential Scanning calorimetry, DSC), NMR relaxation study, or standard analytical titration (indexed by Iodine Value, also know as IV value refer ASTM D5768-02 and DIN 53241). Whether referring to the amounts of C=C double bonds or ratio of saturated/unsaturated fatty acids in triglycerides, IV value is a good easy way to identify saturated triglycerides (e.g., the lower the IV value, the more saturated).

In this application, applicants claim compositions having a critical window (e.g., 1 to 15%, preferably 2 to 10% by wt.) of partially hydrogenated triglyceride (whether introduced as single component or as mixture with other oils) which allow retention of stability for personal wash formulations. When noted amounts are used, personal wash compositions retain a defined percent of original viscosity. The partially hydrogenated triglycerides of defined IV contain a level of saturation yielding high melting point at room temperature. In applicants' copending application, critical window (amounts and defined IV) of hydrogenated triglycerides which have a level of saturation providing similar stability.

BACKGROUND

Personal wash compositions seek to provide consumers additional skin conditioning benefits beyond simple cleansing. The principal benefits provided by such compositions are mildness and moisturization. Because of their low cost, smooth sensory feel and mildness to skin, emollient oils such as triglyceride based vegetable oils (e.g., soybean oil, sunflower seed oil) and fatty acids are among the most commonly used skin benefit agents.

Emollient oils such as triglycerides and long chain fatty acids can penetrate or deposit onto skin from personal wash application to retard skin dehydration and alleviate the irritation or lipid/protein damage from surfactants. The emollient oils play these roles in body wash products because of their intrinsic water insoluble property (hydrophobicity). However, the oil phase in liquid cleansing formulations can challenge formulation stability because of the incompatibility between the aqueous continuous phase and the water immiscible oil phase. High levels of surfactants and/or emulsifiers are frequently used to stabilize the interface between the water phase and oil phase to to help stabilize the formulations.

A problem in the art is how to provide long term stability over a wide range of transportation/storage temperatures. Surfactant based liquid cleanser formulations use different structuring technologies to form stable formulations. Simple isotropic formulations, for example, can be stabilized using high concentrations of surfactant. More complex liquid cleansing formulations, which may contain substantial amounts of skin beneficial agents, use other structuring agents such as suspending polymer, fibers, starch, or solid long chain ($>C_{12}$) fatty acids to help stabilize the formulations. In order to form a stable and consistent body wash product, usually the composition needs to be formulated at a temperature higher than the melting point of all ingredients in the compositions so that the highest melting solid ingredient can evenly distribute into the surfactant phase. When the temperature decreases below their melting point, however, the contained solid ingredients generally crystallize. Often, small crystal particles grow and precipitate out from the surfactant phase. This can cause both product phase separation and significant viscosity drop. Where the temperature is even lower than the Kraft point of the surfactant phase, co-crystallization of solid fatty acid and surfactant may occur when using solid hydrophobic ingredients.

In applicants' copending U.S. Ser. No. 12/371,050, filed in February 2009, there is disclosed a method of using fully hydrogenated triglyceride oil as a structuring agent to modify the rheology of liquid triglyceride oils. It was found that, within specifically defined ratios of hydrogenated triglycerides to liquid oils, an oil mixture of regular liquid vegetable oils and its hydrogenated derivatives could match the shear thinning property of petrolatum gel and have a negligible impact on the foaming property of liquid cleansing formulations. That reference does not disclose use of critical amounts of partially hydrogenated oils of defined IV delivered where partially hydrogenated triglyceride is the sole component or were partially hydrogenated triglycerides is used in a mix with other oils (if it is used in a mixture, 50% or more of mix is the defined partially hydrogenated triglyceride). Further there is no recognition of the benefit (e.g., the stability) provided by the partially hydrogenated triglycerides and/or mixtures of our invention.

Unexpectedly, applicants have now found that, if used within defined window of 1% to 15% by wt., preferably 2 to 10% partially hydrogenated triglyceride oils (delivered as sole component or as mixture where partially hydrogenated triglyceride of defined IV comprises 50% or more, preferably 60% or more of the mixture), the partially hydrogenated triglycerides stabilize the oil/water interface of liquid products containing fatty acid and thus stabilize the liquid cleansing formulations over a wide range of storage temperature, even temperatures as low as 4° C.

The present invention discloses liquid cleansing compositions comprising defined amounts of partially hydrogenated triglyceride to stabilize the compositions over a temperature range of 4° C. to 50° C. The partially hydrogenated triglycerides can be sourced from commercially available products which are partially hydrogenated triglycerides where naturally sourced vegetable oils are partially hydrogenated by catalyst used to control the degree of saturation. It is critical that total amounts of partially hydrogenated glycerides in the final composition be within specific amount range to ensure retention of viscosity after cold temperature storage (4° C. for one week). Use of such critical window of partially hydrogenated triglyceride in liquid cleansing compositions, preferably, compositions comprising fatty acyl isethionate and amphoteric; or acyl isethionate and alkanoyl glycinate is believed unknown.

In general, triglycerides are the main constituents of vegetable oils and animal fats. A triglyceride, also called triacylglycerol (TAG), is a chemical compound formed from one molecule of glycerol and three fatty acids. Hydrogenated triglycerides are the triglyceride oils produced after the contained unsaturated double bonds are hydrogenated and converted into single bonds. The schematic chemical structure of hydrogenated triglycerides is given below:

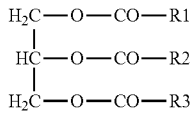

where R1, R2, R3 are saturated carboxylic acids which are esterified with glycerol to form saturated triacylglycerol (TAG) esters. The fatty acids in TAG commonly have chain lengths from 10-24, mostly including C10 (Capric acid), C12 (Lauric acid), C14 (Myristic acid), C16 (Palmitic acid), C18 (Stearic acid) and C20 (Arachidic acid) fatty acid. Naturally sourced vegetable oils and fats also contain substantial amount of monounsaturates such as C16:1 (Palmitoleic acid), C18:1 (Oleic acid) and polyunsaturated fatty acids such as C18:2 (Linoleic acid)) and C18:3 (Linolenic acid) and so on, depending on the source of oils and regions. In the oil and grease industry, the hydrogenated triglycerides are synthesized by catalyst induced addition reaction with hydrogen to remove the C═C double bonds in fatty acid chains. The degree of saturation in triglycerides can be quantified by the amount of contained double bonds in the molecule. Conveniently, the Iodine Value (or "iodine adsorption value" or "IV number" or "iodine index") is often used in lipid chemistry, and is defined as the mass of iodine in grams that is consumed by 100 grams of a chemical substance. For triglycerides, a higher iodine value indicates more unsaturated double bonds in fatty acids. In an ideal case, a fully hydrogenated triglyceride should have Iodine value close to zero as it can not be further reacted with hydrogen. Also, by the definition of Iodine Value, this should be the case for all types of triglyceride oil.

Besides Iodine Value, the solid content (crystal percentage) is another frequently used parameter used to characterize partially hydrogenated triglycerides, whether added alone or as a mixture. Thermal transition analysis (Differential Scanning calorimetry, DSC) is used to measure the contained crystal content by calculating from the energy (enthalpy) needed to achieve phase transition of samples (melting for crystal phase or freezing for liquid phase). In DSC, the crystal percentage is calculated by the integrated melting (or freezing) peak of samples as compared to the fully hydrogenated samples of the same oils. At room temperature, hydrogenated triglyceride (usually have melting point much higher than room temperature), would have 100% crystal percentage while liquid oils have 0% crystal percentage and partially hydrogenated triglyceride or oil mixture have a value in between.

There has been much work relating to use of hydrogenated triglycerides and structured oils in personal product composition. Some of the most relevant works are briefly listed as following:

EP 1,479,365 discloses benefit agent materials structured with crystalline material. U.S. Publication 2004/023569 A1 discloses non-bar compositions comprising crystalline wax structured benefit agent. U.S. 2004/0234467 A1 discloses compositions comprising structured benefit agent for deposition of hydrophilic benefit agent. EP 1,479,378 relates to bars with crystalline wax structured delivery vehicle.

U.S. 2004/0234468, U.S. 2004/0234469 and U.S. 2004/0234558 disclose structured premix to enhance delivery of hydrophobic agent.

WO 2004/017745 discloses mixing non-hydrogenated and hydrogenated oils for dispersed liquid oil or solid particles in fat phase for food compositions.

None of these references disclose compositions wherein specific critical amounts (1 to 15%) of partially hydrogenated triglyceride oil having defined IV value are used in combination with defined fatty acids to stabilize liquid compositions over low temperature storage conditions.

U.S. 2005/0281851 to Cap discloses cosmetic products comprising vegetable oil to blends and additional fatty acid where blends have iodine value range of 20-80, and where no applicable viscosity range is specified. There is no disclosure of use of 1 to 15% of partially hydrogenated triglyceride alone or as mixture with other oil where partially hydrogenated triglyceride of defined IV (e.g., 40 to 100) comprises 60% or more of mixture, or of advantageous use for low temperature stability. Further, Cap does not disclose use of our stabilizing system in personal wash compositions, particularly phase comprising DEFI surfactant, and amphoteric surfactant or DEFI surfactant and alkanoyl glycinate surfactant.

Unexpectedly, applicants have found that when specific range of partially hydrogenated triglyceride of defined IV value is used in liquid compositions comprising $C_{10}$-$C_{20}$ linear fatty acids, low temperature stability (as low as 4° C. for one week) is retained (75% or greater viscosity).

BRIEF DESCRIPTION OF INVENTION

The present invention relates to personal product composition with low temperature stability and retention of viscosity comprising:
(1) 1 to 40 wt. %, preferably 5 to 40%, more preferably 10 to 35% of surfactants containing mixture of anionic, nonionic, zwitterionic surfactants and mixture of the above
(2) 0.5 to 5 wt. % linear fatty acids with 10 to 20 carbons
(3) 1 to 15, preferably 2 to 10 wt. % of partially hydrogenated triglyceride with IV number 20 to 100, preferably 40 to 100, more preferably 50 to 90, even more preferably 60 to 80 and a melting temperature between 35° C. to 80° C.;
wherein said partially hydrogenated triglyceride is introduced alone or as a mixture with other oils (wherein the partially hydrogenated triglyceride of defined IV comprises 50% or more, preferably 55% or more, more preferably 60% or more of such mixture);

wherein said liquid cleanser composition is stable at low temperature and retains at least 70%, preferably 75% or greater of its original viscosity after being stored at 4° C. refrigerator for 7 days.

As noted, total partially hydrogenated triglyceride of IV 40 to 100 is delivered as alone, or as mixture with other oils.

The invention further relates to a method of stabilizing liquid composition at temperatures of 0° to 50° C., preferably 4 to 40° C. which method comprises utilizing the composition noted above.

In a preferred embodiment the partially hydrogenated triglyceride mixture is used alone and comprises 2% to 15%, preferably 3% to 10% of the personal wash composition.

The viscosity results of products stored at 4° Celsius for 7 days are summarized in the examples. These clearly indicate that partially hydrogenated triglyceride, as claimed in the invention, can improve the low temperature stability of the liquid cleanser composition. For example, Comparative Example B having no partially hydrogenated triglyceride oil mixture in the liquid, retained only 51.9% of the original viscosity (34800 cps vs. 73200 cps overnight viscosity) after being stored at 4° C. for 7 days. Liquids with the same surfactant composition as Comparative Example B, but containing the partially hydrogenated triglyceride oil of this invention (Examples 1 and 2) were stable at low temperature, and maintained 80% or more of their original viscosity. Comparative Example C containing partially hydrogenated soy with IV number 104, higher than the desired number of this invention, retains 34.5% or original viscosity.

For mixture of partially hydrogenated triglycerides with other benefit oils there is still required presence of 1 to 15% (total composition) partially hydrogenated oil. Further, to ensure the concentration of crystal content is sufficient to ensure stabilization, the partially hydrogenated triglyceride comprises 50% or more, preferably 60% or more, even more preferably 70% or more, even more preferably 80% or more of the mixture.

The use of blend in liquid surfactant containing personal product compositions allows use of triglyceride to stabilize liquid cleansing products at low temperature during storage and transportation.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

BRIEF DESCRIPTION OF THE FIGURES

FIG. 2 is a graph demonstrating the dependency of measured melting enthalpy of a mixture of partially hydrogenated oil mixture (partially hydrogenated soybean oil mixture) and the mean iodine value as calculated from range of IV provided by suppliers of the mixtures.

DETAILED DESCRIPTION OF THE INVENTION

Figure 1:
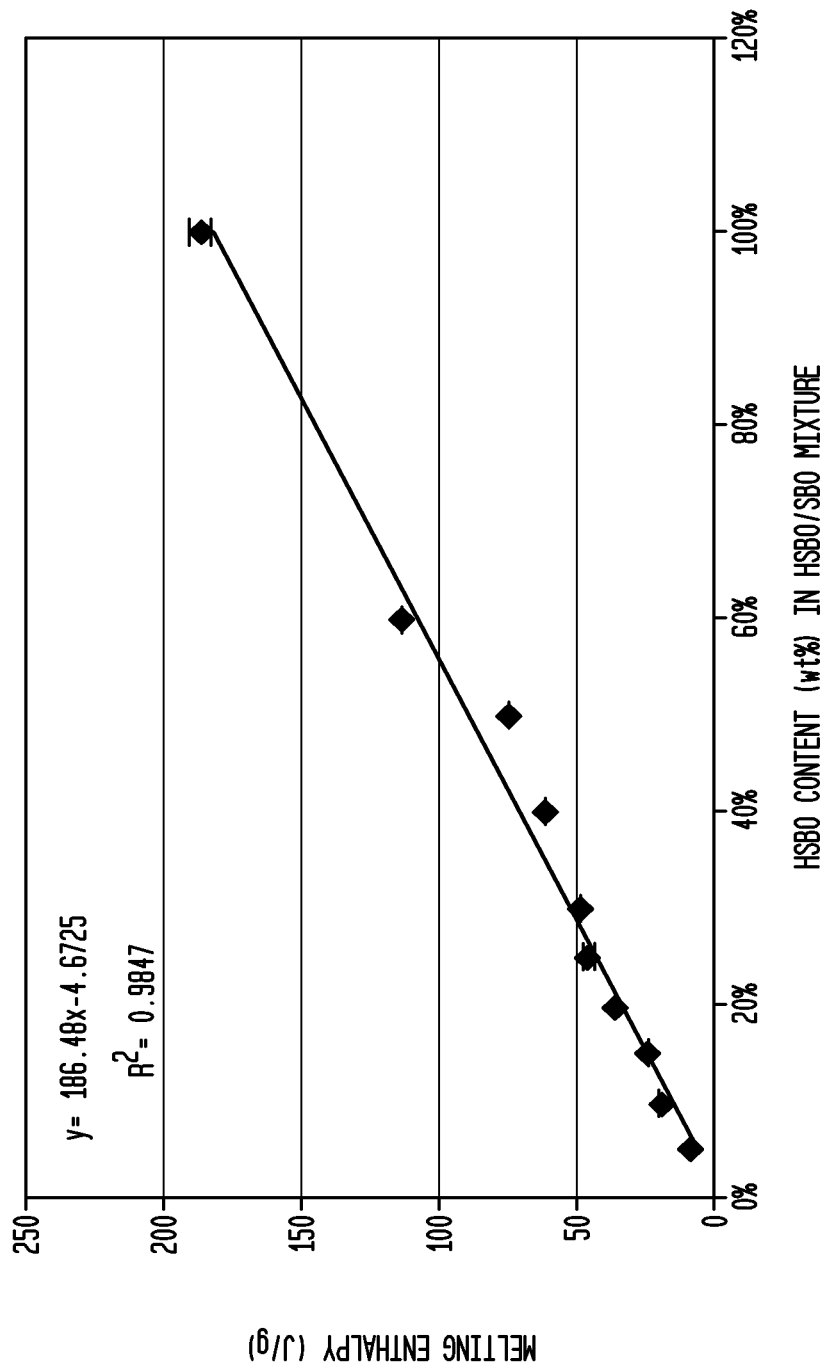
FIG. 1 is a graph demonstrating that DSC methodology can be used to show the correlation (e.g., linear) between, on the one hand, the melting enthalpy of a mixture of fully hydrogenated oil (hydrogenated soybean oil or "HSBO") and additional oil (e.g., regular soybean oil or "SBO"); and, on the other hand, the amount of HSBO in such mixture. The amount of HSBO in the mixture (function of melting enthalpy) is a measure of the crystallinity of the oil mixture.

The present invention relates to surfactant-containing liquid (also containing linear fatty acids) personal wash compositions (preferably aqueous based compositions having >30%, preferably 35% water) providing low temperature stability (retention of viscosity after cold temperature storage) using specific amount of partially hydrogenated triglyceride having a defined degree of saturation. Specifically, when a defined partially hydrogenated triglyceride (defined by specific iodine value) is specifically formulated with surfactants and other ingredients, the compositions will have precisely the right characteristics such that the low temperature stability of liquid formulations is retained. The partially hydrogenated triglyceride may be delivered as pure component (i.e., only partially hydrogenated triglyceride having defined IV range is used), or the partially hydrogenated triglyceride may be delivered as component in combination with other oils (i.e., oil which may have IV range outside defined range). It is important however that there be present sufficient partially hydrogenated triglyceride component in the overall formulation such that formulations retain greater than 70%, preferably 75% or greater, of their original formulation viscosity value after storage at 4° C. for 7 days. As noted, this results from the use of sufficient partially hydrogenated triglyceride whether delivered alone or mixed with other oils. The partially hydrogenated triglyceride (having IV number of 20 to 100, preferably 40 to 100, more preferably 50 to 90) should be used in amount 1 to 15%, preferably 2 to 10% by wt. total composition to obtain the required low temperature stability characteristics noted in compositions of the invention.

In general, degree of saturation/hydrogenation may be characterized (1) by an iodine value which corresponds to that specific value for a particular oil; (2) by phase transition enthalpy; and (3) by the concentration of hydrogenated triglyceride crystal percentage. The invention is described in greater detail below.

The compositions in which the blends of the invention may be used comprise 1% by wt. to 40% by wt., preferably 5 to 40%, more preferably 10 to 35% by wt. surfactant. Surfactants may be anionic, nonionic amphoteric/zwitterionic, cationic or mixtures thereof. Examples of the many surfactants which may be used are set forth, for example, in U.S. Pat. No. 6,395,690 to Tsaur.

Anionic may be aliphatic sulfonate (e.g., $C_8$-$C_{22}$ alkane or alkene sulfonate or aromatic sulfonate); alkyl sulfate (including alkyl and alkyl ether sulfate); sulfosuccinate; taurate; sarcosinates; sulfoacetate; alkyl phosphate.

Anionics may also be carboxylates and ether carboxylates. Another preferred class is $C_8$ to $C_{22}$ acyl isethionates. These esters are prepared by reacting alkali metal isethionate with mixed aliphatic fatty acids. In a preferred embodiment, the isethionate surfactant comprises 5 to 25 wt %, preferably 8 to 20 wt % of the composition.

In a preferred embodiment of the invention, anionic surfactant comprises 50% or more of the surfactant system of the composition of the invention.

Zwitterionic surfactants are broadly derivates of aliphatic quaternary ammonium, phosphonium and sulfonium compound in which aliphatic radicals are straight or branched chain, and wherein one of the aliphatic substituents contains 8 to 18 carbons and one contains an anionic group, e.g., carboxy, sulfonate, sulfate, phosphate or phosphonate.

Amphoteric surfactants include at least one acid group (e.g., carboxylic or sulphonic acid group). They include quaternary nitrogen and are quaternary amido acid. They typically include $C_7$ to $C_{18}$ alkyl or alkenyl group. Examples include betaines, amido betaines, sulphobetaines.

The surfactant system may also optionally comprise a nonionic surfactant.

The nonionic which may be used includes in particular the reaction products of compounds having a hydrophobic group and a reactive, hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference. Preferred alkyl polysaccharides are alkylpolyglycosides.

Cationic surfactants are selected from the group consisting of: alkyl trimonnium chloride and methosulfate, and dialkyldimonnium chloride and methyl sulphate, and alkyl alkonium chloride and methyl sulphate and mixtures thereof. These surfactants contain $C_{12}$ to $C_{24}$ carbon atoms per alkyl chain. The most preferred cationic is selected from the group consisting of stearylalkonium chloride, stearyltrimonium chloride. Di-stearyl-dimonium chloride, and mixtures thereof.

A particularly preferred composition in which triglycerides of the invention may be used comprises 1 to 25 wt %, preferably 1 to 20 wt % DEFI (directly esterified fatty acid isethionate) and 1 to 15 wt % other synthetic cosurfactants, especially betaine and glycinate cosurfactants.

In another preferred embodiment, the compositions may comprise a combination of a fatty acyl isethionate product and alkanoyl glycinate. An example of such system is described, for example, in U.S. Ser. No. 12/751,049 to Tsaur et al., filed Mar. 31, 2010, hereby incorporated by reference into the subject application.

A preferred fatty acyl isethionate product might comprise (in addition to other components) both pure fatty acyl isethionate surfactant (e.g., 40 to 80% of the product) as well as free fatty acid and/or fatty acid salt (e.g., 15 to 50%). In addition, in such preferred product, greater than 20%, preferably greater than 25% of the fatty acyl isethionate and less than 45 wt. % may be of chain length greater than or equal to $C_{16}$; and greater than 50%, preferably greater than 60% of the free fatty acid/soap may be of chain length $C_{16}$ to $C_{20}$.

The fatty acyl isethionate surfactant component is typically prepared by the reaction of an isethionates salt such as alkali metal isethionates and an aliphatic fatty acid having 8 to 20 carbon atoms and Iodine Value (measuring degree of unsaturation) of less than 20 g, for example:

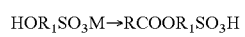

$HOR_1SO_3M \rightarrow RCOOR_1SO_3H$ where $R_1$ is an aliphatic hydrocarbon radical containing 2 to 4 carbons;

M is alkali metal cation or metal ion (e.g., sodium, magnesium, potassium, lithium), ammonium or substituted ammonium cation or other counterion; and R is an aliphatic hydrocarbon radical having 7 to 24, preferably 8 to 22 carbons.

Depending on the processing conditions used, the resulting fatty acyl isethionate product can be a mixture of 40 to 80% by weight of fatty acyl isethionates (which formed from the reaction) and 50 to about 15 wt. %, typically 40 to 20 wt. % of free fatty acids. In addition, product may contain isethionates salts which are present typically at levels less than 5 wt. %, and traces (less than 2 wt. %) of other impurities. Preferably, a mixture of aliphatic fatty acids is used for the preparation of commercial fatty acyl isethionates surfactants. The resulting fatty acyl isethionate surfactants (e.g., resulting from reaction of alkali metal isethionate and aliphatic fatty acid) preferably should have more than 20 wt. %, preferably more than 25%, but no more than 40% wt., preferably 35% (on basis of fatty acyl isethionates reaction product) of fatty acyl group with 16 or greater carbon atoms to provide both lather and mildness of the resulting fatty acyl isethionate product. These longer chain fatty acyl isethionate surfactants and fatty acids, i.e. fatty acyl group and fatty acid with 16 or more carbons, form insoluble surfactant/fatty acid crystals typically in water at ambient temperatures. While not wishing to be bound by theory, it is believed that long chain fatty acyl isethionate surfactants in the product together with free long chain fatty acids in the product contribute to the mildness of the fatty acyl isethionate product for skin cleanser applications.

Examples of commercial fatty acyl isethionate products that are particularly useful in the subject invention are DEFI flakes and Dove® cleansing bar noodles produced by Unilever. DEFI (Direct Esterification of Fatty Isethionate) flakes typically contain about 68 to 80 wt. % of sodium fatty acyl isethionate and 15 to 30 wt. % free fatty acid. More than 25 wt. % and no more than 35% of fatty acyl group of the resulting fatty acyl isethionate have 16 to 18 carbon atoms. Dove® cleansing bar noodles are mixtures of DEFI flakes described above and long chain (mainly $C_{16}$ and $C_{18}$) fatty acid and fatty soap which contain about 40 to 55 wt. % of fatty acyl isethionate and 30 to 40 wt. % of fatty acid and fatty soap. Due to the high level of long chain (16 or more carbons) fatty acyl isethionate and fatty acid, these preferred fatty acyl isethionate surfactant products are extremely mild and have very good emollient benefits to the skin.

The alkanoyl glycinate used is typically a salt of alkanoyl glycinate. Preferred salts include alkali metal salts of alkanoyl glycinate such as sodium cocoyl glycinate and/or alkanolamino salts such as trialkanolamine salt of glycinate.

As is well know in the art, alkanoyl is the systematic name for group:

which is also known as an acyl group. Thus, alkanoyl glycinate is the same as acyl glycinate and represents a molecule, for example, where salt of acyl group, such as for example:

(where R may be, for example, $C_8$-$C_{24}$, preferably $C_{12}$-$C_{20}$) is combined with glycine:

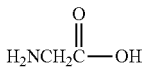

to form the alkanoyl glycinate (an amide where alkanoyl group bonds to nitrogen to form amide):

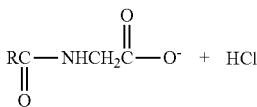

The above reaction may be conducted, for example, by an acid chloride route where R group on the acyl chloride is used to define the R group on the final alkanoyl glycinate (e.g., cocoyl glycinate if R in the acyl group is a cocoyl group).

In another preferred embodiment of the invention composition of the invention further comprise a $C_{10}$ to $C_{20}$ straight chain fatty alcohol, for example, lauryl alcohol. Even in absence of partially hydrogenated triglycerides, it appears to help stability. In the presence of the defined partially hydrogenated triglyceride, it seems to have quite strong stabilizing effect. Fatty alcohol may be used in an amount of 0.05 to 5%, preferably 0.1 to 3%, more preferably 0.2 to 1.5% by wt.

A second component of the invention is $C_{10}$ to $C_{20}$ linear fatty acids. These typically can cause instability in liquid compositions, particularly those stored in cold climates. Compositions of the invention comprise 0.5 to 10%, preferably 1 to 8% by wt. of said fatty acids. The linear fatty acids of the invention may be introduced directly or may be introduced as part of the DEFI product which product contains both acyl isethionate and fatty acid components.

A third required component of the subject invention (besides (1) surfactants and (2) linear fatty acid) is partially hydrogenated triglyceride oil. More specifically, the invention requires that there be used from 1 to 15% by wt. (total content whether delivered alone or as mixture with other oils) of partially hydrogenated oil which has IV number of 40 to 100, preferably 50 to 90 and a melting temperature between 35° to 80° C. (reflective of level of saturation).

As indicated, the partially hydrogenated triglycerides of defined IV value and concentration in the composition are required to give low temperature stability and viscosity retention. However, as also noted, the partially hydrogenated triglycerides can be delivered in combination with other oils (e.g., vegetable oils such as soybean oil or sunflower seed oil, or hydrocarbon oils such as mineral oil or petrolatum jelly) as long as the defined partially hydrogenated triglyceride comprises 60% or more of the mix. Where the other oil has a much higher IV number (for example, pure soybean oil has IV of about 120-140), the IV of a mix of such oil and partially hydrogenated triglyceride may be higher than 100 (because of high levels of polyunsaturated fatty acids in the other oil). However, as long as there is present 1 to 15% of the partially hydrogenated triglyceride (providing required crystallinity) such than the composition retain >70%, preferably 75% or more of the original viscosity, low temperature instability is controlled.

In a second embodiment of the invention, the invention relates to a method of stabilizing liquid composition which can be stored at a temperature of as low as 4° C. for one week which method comprises using a composition comprising:
 a. 1 to 40%, preferably 5 to 35% by wt. surfactant as defined above;
 b. 0.5 to 5% by wt. linear fatty acid of chain length $C_{10}$-$C_{20}$; and
 c. 1 to 15%, preferably 2 to 10% by wt. of partially hydrogenated triglyceride oil having IV 20 to 100, preferably 40 to 100 and having melting temperature below 35° to 80° C.

wherein said partially hydrogenated oil is introduced alone (typically it will have sufficient crystallinity to be solid rather than liquid) or as a mixture of defined partially hydrogenated oil and other oils as long as total content of hydrogenated oil in total formulations is 1 to 15% such that formulation will retain greater than 70%, preferably 75% or more of original viscosity after storage stability evaluation.

Protocol

1. Sample Preparation

Liquids were prepared by mixing all the ingredients except glydant plus, perfume, citric acid and EDTA at 70-75° C. for 30 to 50 minutes until all the solids such as lauric acid, hydrogenated triglyceride and fatty acyl isethionate surfactant product dissolved to form a uniform mix. Fatty isethionate product is fatty acyl isethionate products manufactured by Unilever. It contain about 50 wt % of fatty acyl isethionate surfactant with about 30% of the fatty acyl group equal to or longer than 16 carbon, and about 35 wt % of linear fatty acid/linear fatty soap in which about 79 wt % of the fatty acid/fatty soap have 16 to 20 carbons. Partially hydrogenated triglyceride oil was added as is to the mixing tank; or added as a premix with other triglyceride oil by mixing the partially hydrogenated triglyceride oil with other oils, such as sunflower seed oil, above the melting temperature of the partially hydrogenated triglyceride oil. The mixture was then cooled below 40° C. Rest of the ingredients were added and mixed for another 10 to 20 minutes. The sample was poured and saved in 4 ounce jar for viscosity measurement. One was stored at room temperature (20 to 25° C.) and the other was placed in a 4° C. refrigerator for 7 days.

2. Storage Stability Evaluation

The stability of personal wash prototypes were evaluated by viscosity. The viscosity of each sample was measured using viscometer (0.05 rpm, #5 spindle at 20 to 25 C ambient temperature) and the results are also summarized in the table. Overnight viscosity was determined after the sample was aged at 20-25 C room temperature for overnight. 4° C., 7 days storage viscosity was determined after the sample being aged at 20 to 25 C room temperature for 20 to 24 hours after the sample being stored at 4° C. for 7 days.

3. Thermal Transition Analysis

The intrinsic correlation of degree of saturation (indexed by IV number) of triglycerides and the amount of crystalline ingredients present (crystallinity) can be demonstrated by Differential Scanning calorimetry (DSC) method.

For example, in a prepared simple mixture of fully hydrogenated soybean oil (HSBO) with regular soybean oils (SBO), the phase transition enthalpy (measured by DSC) of melting peak is linearly correlated to the amount of fully hydrogenated soybean oil (HSBO) in the mixture (see FIG. 1).

For partially hydrogenated soybean oils containing a mixture of oils with different iodine value, the corresponding melting enthalpy by DSC reveals a similar linear dependence to mean IV number as shown in FIG. 2. The mean IV numbers of such oil mixtures can be calculated from the IV range provided by suppliers of the oil mixtures, while the melting enthalpy obtained by measuring the endothermic peak of crystal melting using standard DSC method.

So for any unknown mixture of triglyceride oils, either a simple mixture of triglyceride oil with fully hydrogenated triglycerides or a commercially obtainable partially hydrogenated triglyceride mixture (obtained, for example, by catalytic reaction), a sample can be identified by iodine value, phase transition enthalpy or crystal content (solid fat index).

Examples 1 to 2 and Comparatives A to C

The viscosity results of products stored at 4° Celsius after overnight and 7 days are summarized in the table. The results clearly indicate that partially hydrogenated triglyceride oil mixture as claimed in the invention can improve the low temperature stability of the liquid cleanser composition. For example, in Comparative Example B, without any hydrogenated triglyceride oil (only sunflower seed oil), the liquid only retained 51.9% of the original viscosity (34800 cps vs. 73200 cps overnight viscosity) after being stored at 4° C. for 7 days. Liquids, with same surfactant composition as Comparative Example B, containing partially hydrogenated triglyceride oil of this invention (Examples 1 and 2), are stable at low temperature, and maintain 80% or more of their original viscosity. Comparative Example C, containing partially hydrogenated soy with IV number 104, higher than the desired number of this invention, is not stable at low temperature. The DSC analysis in FIG. 2 confirmed that this oil does not contain a substantial amount of crystal (melting enthalpy is close to zero) at the applicable temperature range (process, transportation and storage).

Effect of Partially Hydrogenated Triglyceride on Liquid Low Temperature Stability

TABLE 1

| Example<br>Comparative example | 1 | A | 2 | B | C |
|---|---|---|---|---|---|
| Fatty acyl isethionate surfactant product* | 2 | 2 | 2 | 2 | 2 |
| Betaine | 4 | 4 | 4 | 4 | 4 |
| Na laureth (1EO) sulfate | 3.5 | 3.5 | 3.5 | 3.5 | 3.5 |
| Na cocoyl glycinate | 2.5 | 2.5 | 2.5 | 2.5 | 2.5 |
| Lauric acid | 1.75 | 1.5 | 1.75 | 1.75 | 1.75 |
| Pure Gel | 3.85 | 3.5 | 4 | 3.85 | 4 |
| Cationic guar | 0.2 | 0.2 | 0.2 | 0.2 | 0.2 |
| Glycerin | 6 | 6 | 6 | 6 | 6 |
| Soybean oil | — | 0 | — | — | 3 |
| Sunflower seed oil | — | 2.5 | 0 | 5 | — |
| Partially hydrogenated soybean oil (IV = 104) from ADM** | | | | | 5 |
| Partially hydrogenated soybean oil (IV = 70) from ADM** | 5 | 2.5 | 5 | — | — |
| hydrogenated oil addition method | — | added as premix | — | — | added separately |
| glydant plus | 0.2 | 0.2 | 0.2 | 0.2 | 0.2 |
| citric acid | 0.09 | 0.09 | 0.09 | 0.09 | 0.09 |
| Perfume | 1.1 | 1.1 | 1.1 | 1.1 | 1.1 |
| EDTA | 0.05 | 0.05 | 0.05 | 0.05 | 0.05 |
| deionized water | to 100 | to 100 | to 100 | to 100 | to 100 |
| overnight viscosity (centipoise) | 72000 | 71600 | 82300 | 73200 | 101000 |
| 4° C., 7 days storage viscosity (centipoise) | 62000 | 41600 | 77600 | 38000 | 34800 |
| % of original viscosity | 86.1 | 58.1 | 94.3 | 51.9 | 34.5 |

*Product contains about 50 wt. % fatty acyl isethionate surfactant with about 30% of the fatty acyl group equal to or longer than 16 carbons, and about 35 wt. % of linear fatty acid/linear fatty soap in which about 79 wt. % of the fatty acid/fatty soap have 16 to 20 carbons.
**ADM: Archer Daniels Midland Company Example 3-5 and Comparatives D-E More viscosity results for products stored at 4° C. after overnight and 7 days are summarized below. Examples 3 and 4 clearly show use of 10% defined partially hydrogenated triglyceride stabilized composition from low temperature instability compared to use, for example, of 10% soybean oil instead (Comparative D). Example 3 yielded an even higher viscosity retention number than Example 4 after storage at 4° C. for 7 days due to lower IV number and higher crystal content. Example 5 shows that use of 2% defined partially hydrogenated triglyceride has the same stabilizing effect. Comparative E versus Example 5 shows generally the stabilizing effect of fatty alcohol although Example 5 relative to E again shows effect of partially hydrogenated triglyceride.

TABLE 2

| Effect of partially hydrogenated triglyceride | | | | | |
|---|---|---|---|---|---|
| Example | | 3 | 4 | | 5 |
| Comparative Example | D | | | E | |
| Fatty acyl isethionate surfactant product* | 14 | 14 | 14 | 12 | 12 |
| Betaine | 3.5 | 3.5 | 3.5 | 3.5 | 3.5 |
| Na laureth (1EO) sulfate | 5.8 | 5.8 | 5.8 | 8.0 | 8.0 |
| Lauric acid | 2.7 | 2.7 | 2.7 | 2.4 | 2.4 |
| Cationic guar | 0.2 | 0.2 | 0.2 | 0.2 | 0.2 |
| Glycerin | 3 | 3 | 3 | 1 | 1 |
| Soybean oil | 10 | 0 | 0 | 2 | 0 |
| partially hydrogenated soybean oil (IV70) from ADM** | — | 10 | — | — | 2 |
| partially hydrogenated soybean oil (IV76) from ADM** | — | — | 10 | — | — |
| hydrogenated soybean oil addition method | — | separately | separately | — | separately |
| lauryl alcohol | — | — | — | 0.75 | 0.75 |
| glydant plus | 0.1 | 0.1 | 0.1 | 0.13 | 0.13 |
| Perfume | 1.1 | 1.1 | 1.1 | 1.1 | 1.1 |
| Water | to 100 | to 100 | to 100 | to 100 | to 100 |
| EDTA | 0.05 | 0.05 | 0.05 | 0.047 | 0.047 |
| 0.5 rpm overnight | 180000 | 156000 | 148000 | 161000 | 127000 |
| 0.5 rpm 4° C. 4 days | 52000 | 200000 | 132000 | 114000 | 136000 |
| % | 28.9 | 128.2 | 89.2 | 70.8 | 107.1 |

*Product contains about 50 wt. % fatty acyl isethionate surfactant with about 30% of the fatty acyl group equal to or longer than 16 carbons, and about 35 wt. % of linear fatty acid/linear fatty soap in which about 79 wt. % of the fatty acid/fatty soap have 16 to 20 carbons.
**ADM: Archer Daniels Midland Company

The invention claimed is:

1. A liquid cleanser composition for low temperature stability and retention of viscosity comprising:
   1) 5 to 40 wt % of a surfactant system comprising surfactants: selected from the group consisting of anionic, nonionic, zwitterionic surfactants or the mixture thereof,
   2) 0.5 to 5 wt % linear fatty acids with 10 to 20 carbons,
   3) 1 to 15 wt % of partially hydrogenated triglyceride oil mix with IV number 40 to 100, and a melting temperature between 35° C. to 80° C.;
   wherein said partially hydrogenated triglyceride mix is delivered as sole component or as a mixture with other triglycerides where the partially hydrogenated triglyceride mix of specific IV number comprises 60 wt % of or more of overall mixture; and
   wherein, because of the use of partially hydrogenated triglyceride mix with noted IV number alone or in a mixture with other triglycerides wherein the partially hydrogenated mixture comprises 60 wt % or more of such mix, the said liquid cleanser composition is stable at low temperature and retains at least 75% of its original viscosity after being stored at 4° C. refrigerator for 7 days.

2. A composition according to claim 1 wherein surfactant system comprises fatty acyl isethionate product surfactant and alkanoyl glycinate surfactant.

3. A composition according to claim 1 comprising 2 to 10% by weight partially hydrogenated triglyceride mix.

4. A composition according to claim 1 wherein anionic comprises 50% by weight or more of surfactant of 1).

5. A method of stabilizing liquid cleansing composition which can be stored at a temperature of as low as 4° C. for one week which method comprises utilizing composition of claim 1.

* * * * *